United States Patent [19]

Pelosi, Jr.

[11] 4,393,204

[45] Jul. 12, 1983

[54] 3-[[5-(4-CHLOROPHENYL)FUR-FURYLIDENE]AMINO]-5-(SUBSTITUTED)-2-OXAZOLIDINONES

[75] Inventor: Stanford S. Pelosi, Jr., Norwich, N.Y.

[73] Assignee: Norwich Eaton Pharmaceuticals, Inc., Norwich, N.Y.

[21] Appl. No.: 380,823

[22] Filed: May 21, 1982

[51] Int. Cl.³ .......................................... C07D 413/12
[52] U.S. Cl. .................................................. 542/420
[58] Field of Search ........................................ 542/420

[56] References Cited

U.S. PATENT DOCUMENTS 3,678,040  7/1972  Esteve et al. ...................... 542/420

Primary Examiner—Robert W. Ramsuer
Attorney, Agent, or Firm—Anthony J. Franze

[57] ABSTRACT

3-[[5-(4-Chlorophenyl)furfurylidene]amino]-5-(substituted)-2-oxazolidinones are useful as antiinflammatory agents.

3 Claims, No Drawings

3-[[5-(4-CHLOROPHENYL)FUR-FURYLIDENE]AMINO]-5-(SUBSTITUTED)-2-OXAZOLIDINONES

This invention is concerned with chemical compounds and particularly with 3-[[5-(4-chlorophenyl)furfurylidene]-amino]-5-(substituted)-2-oxazolidinones of the formula:

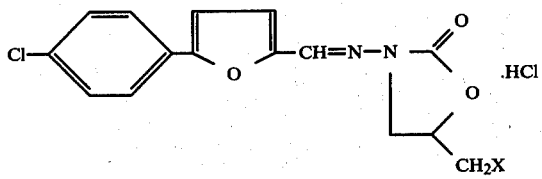

wherein X represents 4-morpholinyl or 1-pyrrolidinyl and a method for their preparation.

These compounds possess pharmacological activity. Particularly noteworthy in this respect is their utility to act as antiinflammatory agents as evidenced by their ability to inhibit edema induced by the administration of carrageenin. Thus, when they are administered orally at a dose of 300 mg/kg suspended in a vehicle such as aqueous methyl cellulose per os to rats receiving carrageenin, edema resulting from that substance is inhibited [Winter et al., P.S.E.B.M. 111:544(1962)].

The compounds of this invention can be combined in various pharmaceutical dosage forms such as capsules, tablets, dragees, suspensions and the like using excipients and adjuvants commonplace in the pharmaceutical art and with which there is no incompatibility.

The compounds of this invention are readily prepared. Currently it is preferred to react the 3-amino-5-(substituted)-2-oxazolidone wherein X represents 4-morpholinyl or 1-pyrrolidinyl with 5-(4-chlorophenyl)-2-furaldehyde in the presence of hydrochloric acid and a solvent such as alcohol.

In order that this invention may be readily available to and understood by those skilled in the art, the following examples are supplied.

EXAMPLE I

3-[[5-(4-Chlorophenyl)furfurylidene]amino]-5-(4-morpholinyl)methyl]-2-ozaxolidinone Hydrochloride A stirring mixture of 10 g (0.05 mole) of 3-amino-5-(4-morpholinylmethyl)-2-oxazolidone, 10.3 g (0.05 mole) of 5-(4-chlorophenyl)-2-furaldehyde and 100 ml of S.D.A. #32 was adjusted to a pH of ca. 3 by the addition of 6 ml of concentrated hydrochloric acid. The reaction mixture was refluxed for 2½ hours, cooled and filtered, obtaining 21 g (100%) of product upon air drying. An analytical sample was prepared by recrystallizing a sample from S.D.A. #30/Darco, m.p. 241°–242° C.

Anal. Calcd. for $C_{18}H_{19}ClN_3O_4 \cdot HCl$: C, 53.53; H, 4.97; N, 9.86. Found: C, 53.46; H, 4.96; N, 9.84.

EXAMPLE II

3-[[5-(4-Chlorophenyl)furfurylidene]amino]-5-[(1-pyrrolidinyl) methyl]-2-oxazolidinone Hydrochloride A mixture of 37 g (0.2 mole) of 3-amino-5-(1-pyrrolidinylmethyl)-2-oxazolidone, 41 g (0.2 mole) of 5-(4-chlorophenyl)-2-furaldehyde, and 800 ml of S.D.A. #32 was adjusted to a pH of ca. 2 by the dropwise addition of 35 ml of concentrated hydrochloric acid. The reaction mixture was refluxed for 3 hours, cooled and filtered to give 78 g of crude product. The 78 g was recrystallized from 3000 ml of S.D.A. #30/Darco and air-dried to yield 44 g (53.8%). An analytical sample was prepared by recrystallizing a sample a second time from S.D.A. #30, m.p. 255°–257° C.

Anal. Calcd. for $C_{19}H_{19}ClN_3O_3 \cdot HCl$: C, 55.75; H, 4.93; N, 10.27. Found: C, 55.49; H, 5.16; N, 10.05.

What is claimed is:

1. A compound of the formula:

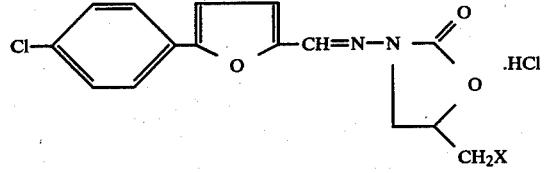

wherein X represents 4-morpholinyl or 1-pyrrolidinyl.

2. The compound 3-[[5-(4-chlorophenyl)furfurylidene]-amino]-5-[(4-morpholinyl)methyl]-2-oxazolidinone hydrochloride.

3. The compound 3-[[5-(4-chlorophenyl)furfurylidene]-amino]-5-[(1-pyrrolidinyl)methyl]-2-oxazolidinone hydrochloride.

* * * * *